United States Patent [19]

Weichselbaum

[11] Patent Number: 4,818,320
[45] Date of Patent: Apr. 4, 1989

[54] NASAL CANNULA HARNESS AND METHOD OF MAKING THE SAME

[75] Inventor: Edwin G. Weichselbaum, Eureka, Mo.

[73] Assignee: Sherwood Medical Company, St. Louis, Mo.

[21] Appl. No.: 882,046

[22] Filed: Jul. 3, 1986

Related U.S. Application Data

[62] Division of Ser. No. 596,754, Apr. 4, 1984.

[51] Int. Cl.⁴ .............................................. B32B 31/00
[52] U.S. Cl. ................................. 156/227; 128/207.18;
128/DIG. 26; 156/215; 156/228; 156/292;
156/293; 156/308.2; 604/94
[58] Field of Search ............... 156/227, 292, 215, 228,
156/293, 308.2; 128/207.18, DIG. 26; 604/94;
29/400 m

[56] References Cited

U.S. PATENT DOCUMENTS

| | | | |
|---|---|---|---|
| Re. 29,487 | 12/1977 | Gardner, Jr. | 128/152 |
| 718,785 | 1/1903 | McNary | |
| 2,647,072 | 7/1953 | Smith | 156/215 |
| 2,735,432 | 2/1956 | Hudson | 128/348 |
| 3,400,714 | 9/1968 | Sheridan | 128/207.18 |
| 3,834,380 | 9/1974 | Boyd | 128/DIG. 26 |
| 3,915,173 | 10/1975 | Brekke | 128/351 |
| 4,156,426 | 5/1979 | Gold | 128/205 |
| 4,367,735 | 1/1983 | Dali | 128/207.18 |
| 4,648,398 | 3/1987 | Agdanowski et al. | 128/207.18 |

FOREIGN PATENT DOCUMENTS 604065 8/1960 Canada ............................... 156/228

Primary Examiner—John J. Gallagher
Attorney, Agent, or Firm—Stanley N. Garber; Andrew J. Beck; William R. O'Meara

[57] ABSTRACT

A nasal cannula harness is provided which includes a pair of sheet members in facing relation and holding the distal end portions of a pair of narine tubes in position for insertion into the nares of a patient. The nasal cannula harness may be made by folding a molded sheet member and securing the sections of the folded member together with the distal portions of the narine tubes between the sections and with portions extending outwardly for insertion into the nares of a patient.

10 Claims, 3 Drawing Sheets

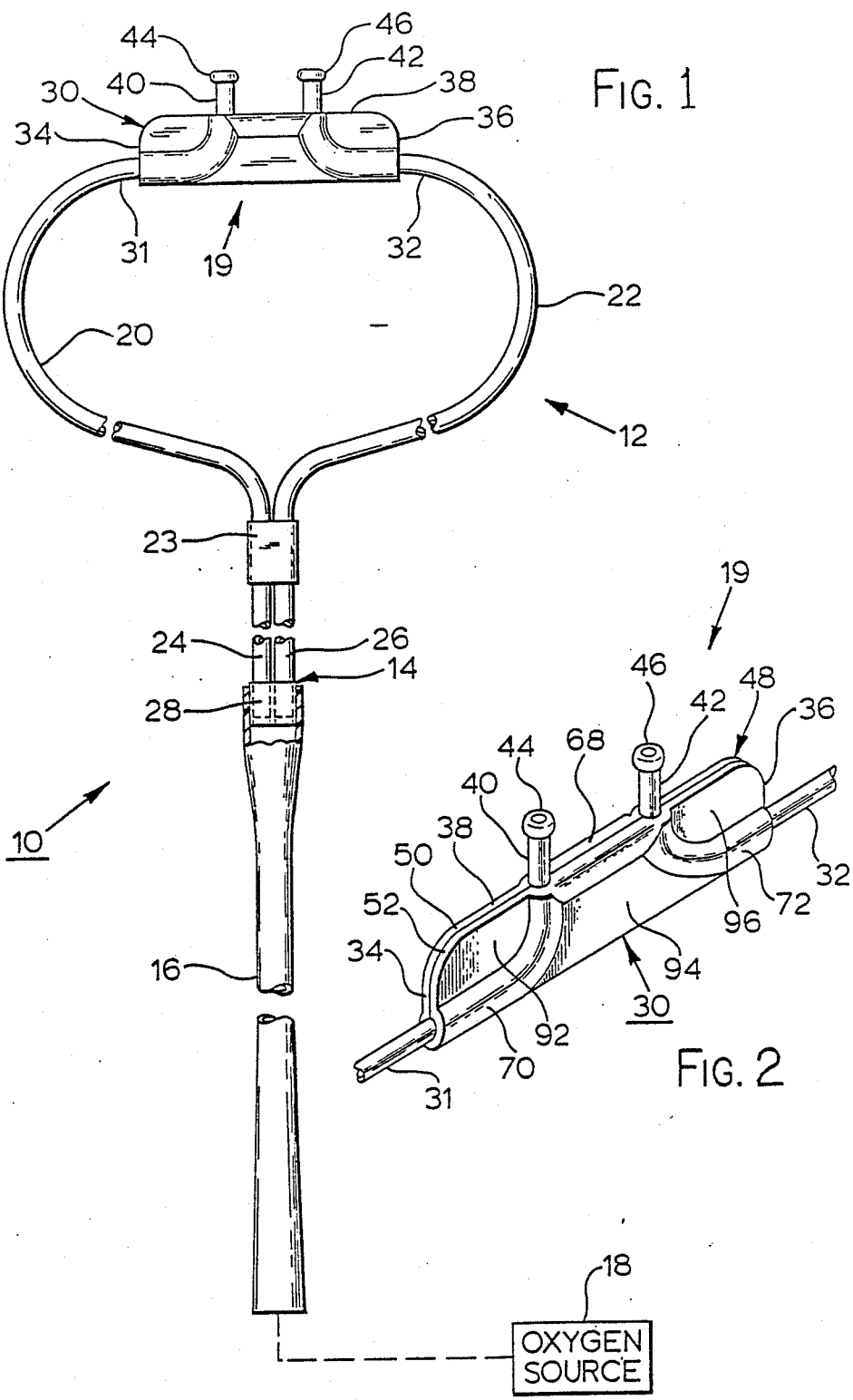

NASAL CANNULA HARNESS AND METHOD OF MAKING THE SAME

This is a divisional of co-pending application Ser. No. 596,754, filed on Apr. 4, 1984.

TECHNICAL FIELD

This invention relates to nasal cannula harnesses for supplying gas to the nasal passages of a patient and to the method of making the same.

BACKGROUND ART

Nasal cannula harnesses which are employed to administer gases, such as oxygen, to the nasal passages of a patient, often require a relatively expensive nasal cannula. For example, a nasal cannual may include a hollow molded bridge member having integrally molded narine tubes and with the bridge member conected to a pair of gas supply tubes. Such hollow bridge members are relatively expensive to mold. In some cases, narine tubes are inserted through holes in a tubular bridge member. With the latter type of bridge, the narine tubes are generally not securely held against relative movement and bending so that there is a possibility that administration gas may be interupted if a tube becomes bent in use. Also, such a tubular bridge member may become so flexible that the narine tubes are difficult to manage or be inserted and maintained within the nares of the patient.

OBJECTS AND SUMMARY OF THE INVENTION

It is therefore an object of the present invention to provide an improved nasal cannula harness having a nasal cannula which is economical in construction and to manufacture, and which overcomes one or more of the above mentioned problems or disadvantages or prior art devices.

Another object is to provide a nasal cannula having an improved bridge for the narine tubes and to an improved method of making the same, and which is simple and economical in construction, and which provides good support for the narine tubes.

In accordance with one aspect of the present invention, a nasal cannula harness is provided which includes a pair of sheet members secured together in facing relation with a pair of narine tubes extending between the sheet members and from one side thereof, the tubes being adapted for insertion into the nares of a patient. In accordance with another aspect of the present invention, a pair of narine tubes are positioned between a pair of sheet members and the sheets members are clamped and secured together in areas on each side of the tubes. In accordance with still another aspect of the present invention, a first section of a sheet member is provided with channels for receiving and locating a pair of narine tubes, and a second section of the sheet member is folded over the tubes and secured in facing relation with the first section to secure the narine tubes between the sections.

These, as well as other objects and advantages of the invention, will become apparent from the following detail description and accompanying drawings.

BRIEF DESCRIPTION OF THE DRAWINGS

FIG. 1 is a plan view of a nasal cannula harness assembly in accordance with a preferred embodiment of the present invention;

FIG. 2 is a prospective view on an enlarged scale of the nasal cannula of FIG. 1;

DETAILED DESCRIPTION OF THE PREFERRED EMBODIMENT

Figure 3:
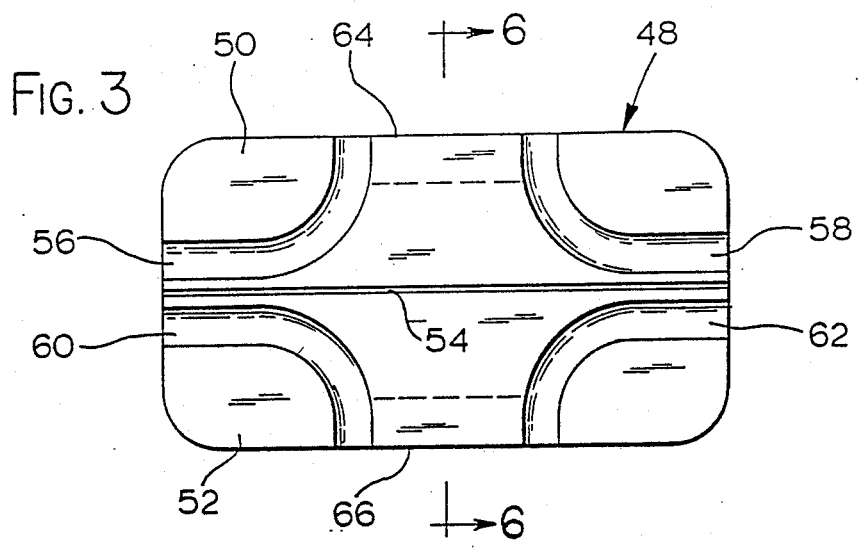
FIG. 3 is a plan view on an enlarged scale of a molded sheet member used in making the nasal cannula of FIG. 1.
Figure 4:
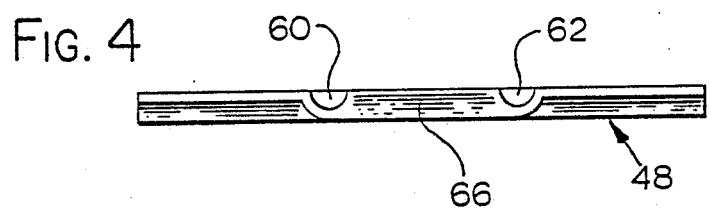
FIG. 4 is a bottom side view of the sheet member of FIG. 3.
Figure 5:
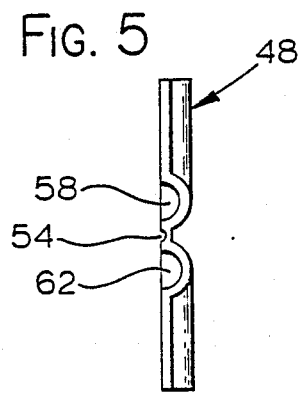
FIG. 5 is a right end view of the sheet member of FIG. 3.
Figure 6:
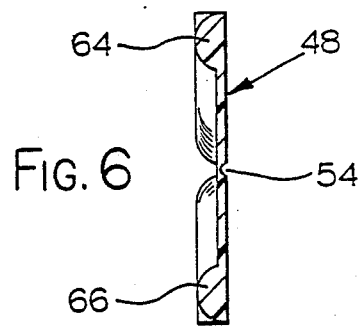
FIG. 6 is a cross-sectional view taken along the line 6—6 of FIG. 3.

Referring now to the drawings, and particularly to FIG. 1, a nasal cannual harness assembly 10 is shown including a nasal cannual harness 12 connected through a tube connector 14 to a main gas supply tube 16 which, in turn, is adapted for connection to a source of gas 18, for example, a source of oxygen or other suitable therapeutic gas.

The nasal cannula harness 12 is shown including a nasal cannula 19, a pair of narine gas supply tubes 20 and 22, and a slip ring 23. The narine tubes have proximal end portions 24 and 26, respectively, connected in sealing relation in a pair of openings extending through a resilient connector plug member 28 of connector 14. Plug 28 may be of rubber or plastic and is shown in fluid tight connection within the distal end of gas supply tube 16. Tube 16 has a greater inner diameter than either of the narine tubes 20 and 22 so as to provide sufficient flow of gas to the nasal cannula harness 12. The nasal cannula 19 includes a bridge 30 connecting distal end portions 31 and 32 of the narine tubes 20 and 22, respectively, in predetermined relationship.

As also is seen in FIG. 2, the distal end portions 31 and 32 of the narine tubes 20 and 22 extend into the opposed ends 34 and 36, respectively, of the bridge 30 and smoothly curve upwardly to and beyond the upper side 38 of the bridge. As shown, the end portions 31 and 32 have external end portions or extensions indicated at 40 and 42, respectively, that are adapted to be received in the nares of a patient. The nare receiving extensions 40 and 42 extend approximately parallel to each other and are shown provided with smoothly rounded, radially outwardly extending rings or flanges 44 and 46, respectively, at the distal ends thereof and provide a desirable fit within the nares of patient when the nasal harness 12 is in use.

The bridge 30 is preferably formed from a unitary or single-piece molded sheet member 48 which is folded back upon itself to provide a pair of facing sheet members or sections 50 and 52 although it is possible to use separate sheet members. The distal end portions 31 and 32 of the narine tubes are clamped between the sheet sections 50 and 52 with the sheet sections secured to one another in areas on opposed sides of each of the tube end portions 31 and 32. The sheet member 48 may be made of rubber or other plastic and is preferably formed of a flexible plastic such as polyvinyl chloride, polyehtylene, or other suitable thermoplastic material.

The sheet member 48 is shown prior to its assembly with the narine tubes in FIGS. 3-7. Member 48 has a longitudinally extending fold groove 54 providing a hinge extending from the left end to the right end of the sheet member, as viewed in FIG. 7, which divides the member into sheet sections 50 and 52. The groove 54 facilitates folding of the sheet member 48 about the narine tubes. As best seen in FIG. 3, sheet section 50 has a pair of grooves or channels 56 and 58 formed in its inner side which extend inwardly from the left and right ends, respectively, of the section and then smoothly curve upwardly to the upper edge of the section. Section 52 also has a pair of grooves or channels indicated at 60 and 62 which extend inwardly from the left and right ends of the section, respectively, and smoothly curve downwardly to the lower edge of the section. The left ends of channels 56 and 60 and the right ends of the chanels 58 and 62 are adjacent the fold groove 54.

The sheet member 48 is shown having a substantially constant thickness throughout except at the fold groove 54 and in areas between the channels and adjacent the upper and lower edges of the sheet member. As seen best in FIGS. 3, 4, 6 and 7, the sheet member is provided with a rounded thickened portion 64 extending longitudinally adjacent the upper edge of the sheet member between the channels 56 and 58. Also, a similar rounded thickened portion 66 is shown extending longitudinally adjacent the lower edge of the sheet member between channels 60 and 62. The rounded portions 64 and 66 in the finished bridge shown in FIG. 2, provide a smoothly rounded nose rest 68 which generally engages the nose of the patient when the harness 12 is in use.

Figure 7:
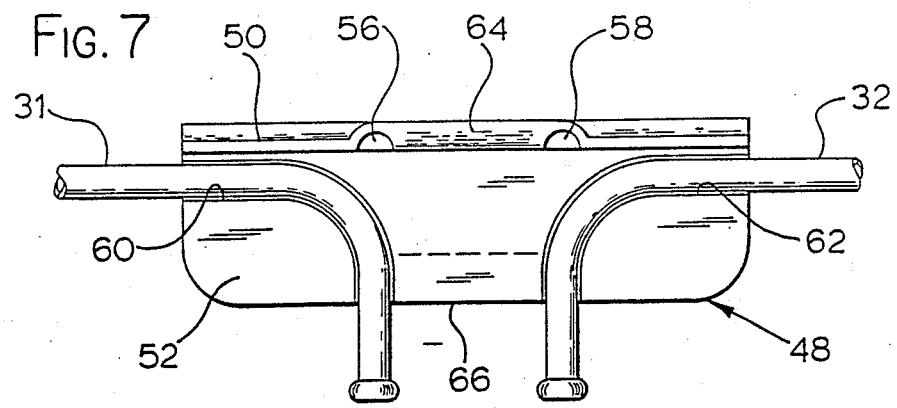
FIG. 7 illustrates a step in the manufacture of the nasal cannula of FIG. 1.

In assembling the bridge 30 with the narine tubes 20 and 22, the distal end portions 31 and 32 may be inserted, for example, into the channels 60 and 62 of sheet member section 52 as shown in FIG. 7. The sheet member 48 is shown partially folded about groove 54 with the upper section 50 at 90° to the section 52. The sheet section 50 may be further folded along fold groove 54 and over the tube sections 31 and 32 with the engaging surfaces or a substantial area thereof secured to the complementary surface of the sheet section 52 to form the assembly as shown in FIGS. 1 and 2. Surfaces of the sheet sections may be secured together (depending upon the material used) by heat welding, solvent bonding, cementing or in other suitable ways. The channels 56 and 60 are complementary and form a tunnel 70 in the bridge (FIG. 2) through which the distal end portion 31 of tube 20 extends, and the complementary channels 58 and 62 form a tunnel 72 through the bridge 30 and through which the distal end portion 32 of narine tube 22 extends.

Figure 8:
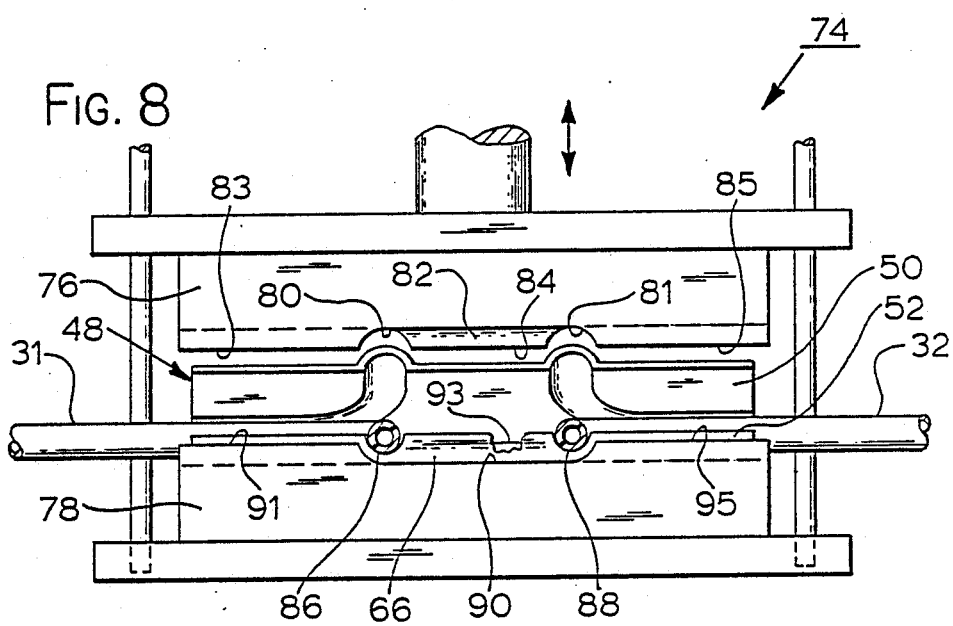
FIG. 8 shows a clamping die assembly which may be used in the manufacture of the nasal cannula of FIG. 1.
Figure 9:
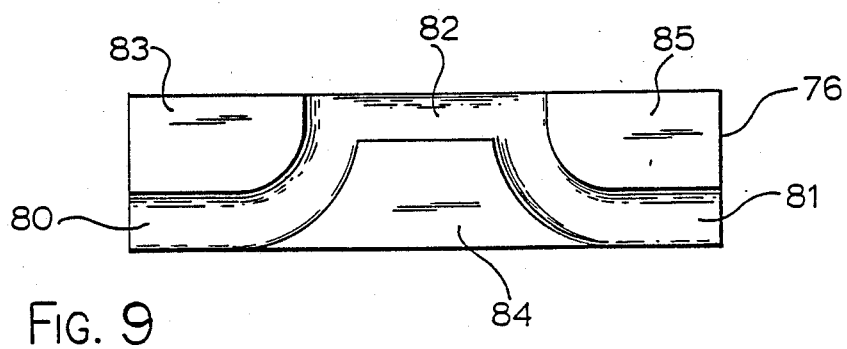
FIG. 9 is a bottom plan view of the upper die member of the clamping die of FIG. 9.

In a preferred method of assembly the sheet member 48 to the narine tubes 20 and 22 to form the completed harness 12, a heat welding die assembly 74 of FIG. 8 may be used. The die assembly 77 includes upper and lower die members 76 and 78 adapted to be heated and which have facing surfaces that are mirror images of each other. The upper die member 76, as shown in FIG. 9, includes a pair of channels 80 and 81 generally complementary to and which receive the channels 56 and 58 of the sheet section 50 during assembly. The die channels 80 and 81 are connected by a longitudinally extending channel or recess indicated at 82 which is complementary to and is adapted to receive the rounded longitudinally extending portion 64 of sheet section 50. The bottom face of die member 76 also has flat heat sealing or welding portions 83, 84 and 85 adapted to engage the flat portions of sheet section 50 during welding. The lower die member 78 includes die channels 86 and 88 for receiving channels 60 and 62 of section 52 and it has a longitudinally extending recess 90 which accommodates rounded portion 66 of the sheet section 52. Die member 78 also has flat heat welding areas 91, 93 and 95 which engage flat portions of sheet section 52 and are complementary to and cooperate with areas 83, 84 and 85 of die member 76 to weld the sections 50 and 52 together.

In using the heat welding die assembly 74, the distal end portions 31 and 32 of the narine tubes may be inserted into the channels 60 and 62 of sheet section 52 as indicated in FIG. 7. The sheet section 50 may be further folded along the fold groove 54 until it forms an acute angle with the sheet section 52. This may be done in the die assembly in some cases, or a partially folded sheet member 48 may be inserted into the lower die member 78 with the channels 60 and 62 of section 52 inserted into channels 86 and 88 of the lower die member 78 as shown in FIG. 8. When the die members 76 and 78 are closed or member 76 is moved downwardly to clamp the sheet sections 50 and 52 together, the channels in the upper and lower die members receive the complementary channels of the sheet member 48, and the rounded portions 64 and 66 are respectively received in channels 82 and 90 of the die members. In this way, the welding portion 83, 84 and 85 of the upper die 76 cooperate respectively with welding portions 91, 92 and 93 of lower die member 78 to engage and heat seal or weld the facing flat areas of the sheet sections together to form the flat portions 92, 94 and 96 (FIG. 2) of the finished bridge 30. The flat welded portions 92, 94 and 96 of the bridge 30 maintain the tubes securely located in the tunnels 70 and 72. Preferably, the tunnels 70 and 72 are sized relative to the size of the narine tubes such that the inner sidewalls of the tunnels frictionally engage the outer surfaces of the tube portions 31 and 32 to maintain them in fixed relationship with the bridge 30. In this way, it is generally not necessary to effect a heat or other bond between the outer surface of the narine tubes 20 and 22 and the inner surfaces of the tunnels 70 and 72 in order to prevent relative movement between the tubes and bridge.

Die assembly 74 may be used, instead of using heat welding, to solvent bond or cement the flat facing surfaces together. Where welding is employed, well known ultrahigh frequency or radio frequency welding may be employed to assemble the bridged and tubes. The inner flat facing sides of the portions 64 and 66 that form the nose rest 68 may also be fixed together.

In use, the two narine tube extensions 40 and 42 are inserted into the nares of the patient with the tubes 20 and 22 generally extending over and behind the ears and downwardly to a point below the chin. The slip ring 23 may be adjusted to provide a desirable harness fit.

The sheet sections of the bridge 30 may be easily and economically molded from flat plastic sheet stock. The bridges are especially economically and simple to make when the bridge sections are of a single unitary molded part such as shown for illustration in the drawings. Also, the assembling of the narine tubes 20 and 22 with the sheet member 48 is simple and economical to perform. The narine tubes in the finished harness are firmly held in the desired location by the tunnels 70 and 72. The sheet member channels forming the tunnels facilitate the manufacture of the nasal cannula harness since the narine tubes may be easily manually bent or curved to fit within the channels. The channels readily predeterminately shape and maintain the distal end portions of the narine tubes in a desired configuration during assembly. While it is preferred to employ sheet members having preformed channels such as sheet members 50 and 52, a pair of sheet members in which there are no preformed channels or where only one of the sheet members is preformed with a pair of channels can be used. When at least one sheet member has a pair of preformed channels, the tubes can be readily located during manufacture; however, the tubes may be held in the shown desired location by any suitable means and unchanneled members used.

The narine tubes 20 and 22, the slip ring 23, and supply tube 16 may be made of any suitable rubber or plastic. For example, they may be extruded from polyvinyl chloride or polyethylene.

As various changes could be made in the above construction and method without departing from the scope of the invention, it is intended that all matter contained in the above description and shown in the accompanying drawings be interpreted as illustrative and not in a limiting sense.

What is claimed is:

1. The method of making a nasal cannula harness for delivering gas to the nasal passages of a patient comprising the steps of providing a pair of flexible narine tubes each having a distal end portion for insertion into a nare of the patient when in use, providing a plastic sheet having left, right, upper, and lower side edges and first and second pairs of channels in one side of said sheet, the first pair of channels extending inwardly from the left and right edges of the sheet, respectively, and curving to the lower side edge of the sheet, the second pair of channels extending inwardly from the left and right edges of the sheet respectively and curving to the upper side edge of the sheet, the depth of the channels being less than the diameter of the narine tubes, and securing the narine tubes to the sheet to form a nasal cannula including the steps of positioning the narine tubes respectively in the channels of one or the pairs of channels with the narine tubes extending out both ends of the said channels and curving generally in accordance with the curves of these channels, folding the sheet into upper and lower sheet sections with the sheet sections in facing relation and such that the channels of the other pair of channels respectively receive the narine tubes and form a pair of tunnels with the channels of said one pair of channels, and fixedly connecting facing portions of the sheet sections on each side of each the narine tubes together to secure the narine tubes relative to the sheet sections.

2. The method of claim 1 wherein securing step includes providing a clamping die having upper and lower die members, positioning the sheet and narine tubes in the die, clamping the upper and lower facing portions of the sheet sections between the die members and bonding the same together.

3. The method of claim 2 wherein said securing step includes heating said die members to heat bond said facing portions.

4. The method of making a nasal cannula harness for delivering gas to the nasal passages of a patient comprising the steps of providing a pair of tubes for conveying gas, providing a pair of sheet members, clamping the sheet members together with end portions of the tubes predeterminately curved and between the sheet members to form a bridge connecting the tube end portions in predetermined relation for insertion into the nares of a patient, the tube end portions being so predeterminately curved and positioned between the sheet members that they extend repsectively into the opposed ends of the bridge and out one of the opposed sides of the bridge for insertion into the nares of a patient when in use, and securing facing areas of the sheet members together on each side of each of the tube end portions to secure the tubes relative to the sheet members.

5. The method claim 4 wherein said sheet members are integrally connected together along the other of the opposed sides.

6. The method of claim 4 wherein said step of securing facing areas of the sheet members together includes clamping the facing areas and heat welding them together.

7. The method of claim 4, wherein at least one of said sheet members has a pair of channels therein, respectively placing the end portions of said tubes in said channels and then securing said sheet members together in facing relation.

8. The method of claim 4 wherein said sheet members are integrally connected together along a fold line recess.

9. The method of claim 8 wherein said securing step includes providing a pair of die members for clamping and bonding together said facing areas of said sheet members.

10. The method of claim 9 wherein said sheet members are of a thermoplastic material, and said securing step includes heating said die members to heat bond said sheet members in said facing areas.

* * * * *